United States Patent
Kobayashi

(10) Patent No.: US 6,605,476 B2
(45) Date of Patent: *Aug. 12, 2003

(54) IMMUNOCHROMATOGRAPHIC ASSAY DEVICE

(75) Inventor: Eiji Kobayashi, Tokyo (JP)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,154

(22) PCT Filed: Apr. 28, 1997

(86) PCT No.: PCT/IB97/00450

§ 371 (c)(1),
(2), (4) Date: Nov. 1, 1999

(87) PCT Pub. No.: WO97/42505

PCT Pub. Date: Nov. 13, 1997

(65) Prior Publication Data

US 2002/0076828 A1 Jun. 20, 2002

(30) Foreign Application Priority Data

May 2, 1996 (JP) .............................................. 8-111744

(51) Int. Cl.$^7$ ............................................ G01N 33/558
(52) U.S. Cl. .......................... 436/514; 422/55; 422/56; 422/57; 422/58; 422/61; 435/287.1; 435/287.2; 435/287.7; 435/287.9; 435/805; 435/810; 435/970; 435/975; 436/169; 436/518; 436/809; 436/810
(58) Field of Search ............................... 422/55–58, 61; 435/287.1, 287.2, 287.9, 805, 810, 970, 975; 436/169, 514, 518, 809, 810

(56) References Cited

U.S. PATENT DOCUMENTS

| | | | | |
|---|---|---|---|---|
| 4,168,146 A | * | 9/1979 | Grubb et al. | 422/56 |
| 4,235,601 A | * | 11/1980 | Deutsch et al. | 422/56 |
| 4,981,820 A | | 1/1991 | Renlund et al. | |
| 5,238,652 A | * | 8/1993 | Sun et al. | 422/61 |
| 5,962,333 A | | 10/1999 | Incorvia et al. | |

FOREIGN PATENT DOCUMENTS

| | | |
|---|---|---|
| EP | 0268410 | 5/1988 |
| EP | 0269410 | 6/1988 |
| EP | 0327395 | 8/1989 |
| EP | 0570188 | 11/1993 |
| EP | 0454437 | 3/1995 |
| EP | 0737468 | 10/1996 |
| FR | 2650269 | 2/1991 |
| GB | 2209496 | 5/1989 |
| JP | 57-77379 | 5/1982 |
| JP | 6230009 | 2/1987 |
| JP | 8026348 | 1/1996 |

* cited by examiner

*Primary Examiner*—Christopher L. Chin
(74) *Attorney, Agent, or Firm*—Regina M. Anderson

(57) ABSTRACT

A chromatography immunoassay device is described which can be used more easily, is protected from moisture and/or oxygen more effectively and can be produced at a lower cost than known chromatography immunoassay devices. The chromatography immunoassay device of the present invention is one in which one or more chromatography strips are stuck on a substrate made of a plate, each of the chromatography strips is sealed by closely adhering a substrate portion surrounding each chromatography strip to a seal film located on the chromatography strip, and the seal film and/or substrate possesses a film containing a dehumidifying agent and/or a film containing an oxygen absorbing agent.

14 Claims, 3 Drawing Sheets

IMMUNOCHROMATOGRAPHIC ASSAY DEVICE

FIELD OF THE INVENTION

This invention relates to chromatography immunoassay devices in which chromatography strips are used. More particularly, the invention relates to a chromatography immunoassay device in which one or more chromatography strips are located on a substrate, each of the chromatography strips is sealed between the substrate and a seal film that entirely covers the chromatography strips, and the seal film and/or substrate is possessed of a film containing a dehumidifying agent and/or a film containing an oxygen absorbing agent.

BACKGROUND OF THE INVENTION

Chromatography immunoassay devices, in which chromatography strips are used, are devices which immunologically detect or measure the presence or quantity of substances to be assayed that are contained in samples, the device having at least a sample adding means and a detecting means. In some cases the chromatography strip also has a labeling means, and such a device is well known and broadly used, as disclosed for example in JP-A-61-145459 (the term "JP-A" as used herein means an "unexamined, published Japanese patent application"), JP-A-1-63865 and JP-W-1-503174 (the term "JP-W" as used herein means an "unexamined, published Japanese international patent application"), all incorporated herein by reference.

Each chromatography strip must be protected by appropriate means, such as packaging, in order to prevent antibodies and like reagents in the chromatography strip from degeneration caused by oxygen, moisture and the like, and to protect the strip itself from pollution caused by touching, or from deformation and the like. Protection by packaging or the like means is effected generally by sticking or putting one or a plurality of chromatography strips on a substrate, putting the resulting preparation into a protective case and then sealing the case in a bag. Alternatively, each chromatography strip is sealed with a laminate film as disclosed in WO 94/24563, incorporated herein by reference. When packed in a bag, the chromatography strip is sealed together with a dehumidifying agent in order to minimize moisture absorption by the chromatography strip.

In the conventional chromatography immunoassay device, however, each chromatography strip requires a protective case, a dehumidifying agent and a package where one chromatography strip is sealed, thus costing much for packaging. In a case in which a plurality of chromatography strips are stuck on a substrate, all of the chromatography strips are packed in a single bag together with a necessary amount of a dehumidifying agent and sealed with a packaging material which is substantially water impermeable. Though this method can reduce the cost required for the packaging material and dehumidifying agent, unsealing the bag to use a first chromatography strip causes exposure of other chromatography strips to the air, or moisture and oxygen, thus posing a problem of causing their deterioration. Thus, it is necessary to take special protective and storage measures, because the stored chromatography strips become useless when they are not properly protected and stored. Case WO 94/24563, incorporated herein by reference, uses chromatography strips which can be isolated from the air, but no additional measures are provided to protect the chromatography strips from moisture and oxygen.

SUMMARY OF THE INVENTION

The present invention resolves the aforementioned problems seen with the prior art chromatography immunoassay devices in terms of their mode and packaging, thereby providing a chromatography immunoassay device which is easier to use, can be isolated from moisture and/or oxygen more effectively, enabling storage over a longer period of time, and that is able to be produced at a lower cost.

A chromatography immunoassay device has been developed which can be used more easily, is protected from moisture and/or oxygen more effectively and has low production cost. This invention is a chromatography immunoassay device in which one or more chromatography strips are located on a substrate, each of the chromatography strips is sealed between the substrate and a seal film that entirely covers the chromatography strips, and the seal film and/or substrate possesses a film containing a dehumidifying agent and/or a film containing an oxygen absorbing agent.

Accordingly, the gist of the present invention resides in a chromatography immunoassay device in which: (1) one or more chromatography strips, having at least a sample adding means and a detecting means, are located at certain intervals on a substrate which is comprised of one plate, with or without a strip support, (2) a seal film that entirely covers the chromatography strips is located on the aforementioned chromatography strip with or without a protective laminate, (3) each of the chromatography strips is sealed by adhering the aforementioned seal film closely to a portion of the substrate around each chromatography strip, (4) the aforementioned adhesion of the seal film to the substrate is effected in such a way that the seal film can be peeled easily from the substrate, at least at the sample-adding area, (5) with regard to the seal film and substrate, (i) either the seal film or substrate has both a film containing a dehumidifying agent and a film containing an oxygen absorbing agent, (ii) the seal film has either a film containing a dehumidifying agent or a film containing an oxygen absorbing agent, and the substrate has the other film, (iii) either the seal film or substrate has either the film containing a dehumidifying agent or the film containing an oxygen absorbing agent, and the other has both the film containing a dehumidifying agent and the film containing an oxygen absorbing agent, (iv) both the seal film and substrate each contain both the film containing a dehumidifying agent and the film containing an oxygen absorbing agent, (v) the seal film and the substrate both contain the same film which is either the film containing a dehumidifying agent or the film containing an oxygen absorbing agent, or (vi) either the seal film or substrate contains either the film containing a dehumidifying agent or the film containing an oxygen absorbing agent, and (6) the seal film and substrate are substantially water impermeable, at least at the portion where the seal film is not adhered closely to the substrate when the seal film and/or substrate has the film containing a dehumidifying agent, and the seal film and substrate are substantially oxygen impermeable, at least at the portion where the seal film is not adhered closely to the substrate when the seal film and/or substrate has the film containing an oxygen absorbing agent.

EFFECT OF THE INVENTION

A chromatography immunoassay device is described which can be used easily, is protected from moisture and/or oxygen and has low production cost. This invention is a chromatography immunoassay device in which one or more chromatography strips are stuck on a substrate made of a single plate, each of the chromatography strips is sealed by closely adhering a substrate portion surrounding each chromatography strip to a seal film located on the aforementioned chromatography strip, and the seal film and/or substrate is possessed of a film containing a dehumidifying agent and/or a film containing an oxygen absorbing agent. Since chromatography strips are isolated from moisture and/or oxygen by the seal film and substrate, they can be stored for a more prolonged period of time. Also, even in the case of a device in which a plurality of chromatography strips are stuck on a substrate, when one chromatography strip is used the remaining chromatography strips are not exposed to air, unlike similar types of conventional devices currently in use. Also, a chromatography strip in the invention herein can be separated from other strips, together with the substrate, without exposing it to air before or after its use. In addition, the chromatography immunoassay device of the present invention does not require labor for packaging which is needed to produce the chromatography strips of the prior art. Thus the strips described herein can be produced at a lower cost.

DETAILED DESCRIPTION OF THE INVENTION

In a chromatography strip, at least a sample adding means and a detecting means are arranged on a chromatography carrier. A sample solution having a possibility of containing a substance to be assayed moves through the chromatography carrier by capillary action when added to the sample adding means, and a labeled substance which is contained in a labeling means arranged on the chromatography strip in advance, or a labeled substance which is added together with the sample solution to the chromatography strip, is accumulated in the detecting means in direct or inverse proportion to the presence or quantity of the substance to be assayed in the sample solution, effected by a immunological reaction, so that the presence or quantity of the substance to be assayed in the sample solution can be found by measuring the presence or quantity of the thus accumulated labeled substance. Various types of chromatography strips are known, and all of these known chromatography strips, including those which will be described later, can be used in the present invention. The term "chromatography immunoassay device" as used herein means a chromatography strip which is produced in such a way that it can be used in an immunoassay and is able to be stored and transported.

The following describes a typical example of the chromatography strip. When a labeling means is present, a sample adding means may be located either at the same place where the labeling means is present or at an upstream position to the labeling means (hereinafter, direction of the movement of a sample solution caused by capillary action is called "downstream" and the opposite direction is called "upstream"), with upstream to the labeling means generally preferred. When a sample solution, having a possibility of containing a substance to be assayed, is introduced into the sample adding means, the sample solution moves through the chromatography carrier in the downstream direction together with the substance to be assayed effected by capillary action. Typically, the substance to be assayed is a compound which binds in a specific fashion to a trapping substance fixed to the detecting means, or it is a compound which binds in a specific fashion to a conjugate that binds specifically to the trapping substance. For example, the substance to be assayed is an antibody when the trapping substance is an antigen or the conjugate contains an antigen, and the substance to be assayed is an antigen when the trapping substance is an antibody or the conjugate contains an antibody.

When the sample adding means is located at an upstream position to a labeling means (a case in which a labeling means is present), the labeling means may be arranged adjacent to the sample adding means or on a position disconnected from the sample adding means. Typically, a labeled substance which binds specifically to a substance to be assayed or binds specifically to a trapping substance in competition with the substance to be assayed is arranged in the labeling means.

When a labeling means is not present, a labeled substance may be added to the sample adding means together with a sample solution, but addition of the labeled substance can be effected by various means for example by adding it to a certain position outside the chromatography strip binding site after addition of the sample solution.

The label may be a radioactive isotope, an enzyme or a colored substance such as gold colloid or the like. These labels are also well known.

Since the labeled substance is arranged in such a manner that it moves by the capillary action of a sample solution, the labeled substance moves in the downstream direction when the sample solution is added to the sample adding means.

The detecting means is generally located at a downstream position from the labeling means and at a certain distance from the labeling means. In the detecting means, a trapping substance which binds only to a substance to be assayed or a conjugate in a specific fashion, or binds specifically to each of the substance to be assayed and a labeled substance, is fixed to the chromatography carrier. Consequently, in one embodiment the substance to be assayed (sometimes linked to a labeled substance), moved by the capillary action of the sample solution, binds to the trapping substance or to a conjugate which in turn binds to the trapping substance. The labeled substance binds to the thus bound substance to be assayed, thereby effecting accumulation of the labeled substance in the detecting means in response to the presence or quantity of the substance to be assayed. Alternatively, the labeled substance and the substance to be assayed, moved by capillary action, bind competitively to the trapping substance or to a conjugate which in turns binds to the trapping substance, thereby effecting accumulation of the labeled substance in inverse proportion to the quantity of the substance to be assayed.

There is a case in which a certain labeled substance binds to both a trapping substance (or a conjugate which in turn binds to a trapping substance) and a substance to be assayed, but not simultaneously and, in that case, the substance to be assayed firstly binds to the labeled substance and the remaining labeled substance which did not bind to the substance to be assayed binds to the trapping substance. In consequence, the presence or quantity of the substance to be assayed can be analyzed by measuring the labeled substance accumulated in the detecting means.

As occasion demands, various substances are located upstream of the detecting means. For example, a conjugate may be so located in a movable manner. A Conjugate is a complex of a compound which binds specifically to a substance to be assayed or a labeled substance and another compound which specifically binds to a trapping substance, and it binds to both the substance to be assayed and the trapping substance or the labeled substance and the trapping substance in a specific manner. Examples of the combination of a compound which specifically binds to a trapping substance and the corresponding trapping substance include biotin and avidin (either could be the trapping substance), an antibody and its corresponding antigen (both having no relation to a sample to be assayed) and the like.

In some cases, one or more additional detecting means may be arranged downstream of the first detecting means. Also, downstream of the detecting means there may be a further extension of the chromatography carrier so that a sample solution can be discharged completely or the carrier may be equipped with a material for use in the absorption of the sample solution.

The chromatography carrier is a carrier of the sample adding means, labeling means and detecting means, which connects these means in such a manner that a sample solution can move by capillary action. A number of materials have been proposed as chromatography carriers, and any of these materials can be used as the chromatography carrier of the present invention. For example, cellulose, nitrocellulose, cellulose acetate and the like are used most frequently as chromatography carriers.

Thus, the presence or quantity of a substance to be assayed in a sample solution can be found by measuring the presence or quantity of a labeled substance accumulated in the detecting means. In one instance, this may be accomplished visually.

As occasion demands, the chromatography strip may be adhered to a strip support in such a manner that one of its sides contacts the strip support (hereinafter, the side in contact with the strip support is called the "rear face" of the chromatography strip). The strip support is used mainly to prevent movement of the sample adding means, labeling means and the like. Sticking of the chromatography strip onto the strip support must be done in such a way that the capillary action of a sample solution in the chromatography carrier is not disturbed so that the sensitivity of detection of a substance to be assayed is not reduced. In some cases, the strip support may be used in such a way that a portion of the sample adding means is not covered.

Also, as occasion demands, a protective laminate may be stuck on the opposite side of the strip support-adhered side of the chromatography strip (hereinafter, this side, or the side opposite to the substrate-adhered side, is called the "front face" of the chromatography strip ). The protective laminate is used mainly to ensure adhesion of the sample adding means and labeling means and to prevent staining and other flaws from occurring to the chromatography strip when used. At least a portion of the protective laminate, where it covers the detecting means, must be transparent, and the sample adding portion of the sample adding means must not be covered by the protective laminate. Sticking of the chromatography strip to the protective laminate must be done in such a way that the capillary action of a sample solution in the chromatography carrier is not disturbed, or so that the sensitivity of detection of a substance to be assayed is not reduced.

Polyethylene terephthalate (to be referred to as "PET" hereinafter) is used most frequently as the strip support and protective laminate; polypropylene (to be referred to as "PP" hereinafter), polyvinyl chloride and the like may also be used.

Adhesion of the chromatography strip to the strip support or protective laminate, or adhesion of the strip support to the substrate which will be described later, may be effected by the use of a rubber, acrylic or vinyl ether polymer adhesive agent.

One or more chromatography strips may be located on a strip substrate with or without the strip support. The term "to locate" as used herein means that the chromatography strips are simply put on the substrate or, in another instance, they are stuck on the strip support, when it is present, or on the substrate, when the strip support is not present. The term "to stick" as used herein means that either the whole surface or just a portion of the chromatography strip is adhered to the substrate. In any case, sticking of the chromatography strip is effective if it does not easily separate from the strip support or substrate during its production or when it is used. In some cases, the substrate may be stuck with paste so that it can be peeled easily from the chromatography strip or strip support.

When the strip support is not used, the substrate may also have the function of the strip support.

When a plurality of chromatography strips are located on the substrate, it is desirable, from the production point of view, to make the downstream and upstream ends of each chromatography strip uniform so that they are parallel. These chromatography strips are located on the substrate and are-a certain distance apart.

The substrate is comprised of a single plate and is stuck on the strip support, when it is present, or on the rear face of the chromatography strip.

The chromatography strip is sealed by closely adhering a seal film, which will be described later, to the substrate at the peripheral area of each chromatography strip located on the substrate, namely the space between chromatography strips when a plurality of the strips are located on the substrate.

The seal film is a sheet of film which can cover the entire portion of the chromatography strip and is located on the chromatography strip with or without the protective laminate.

If the substrate is closely adhered to the seal film by hot sealing, the inner side of the substrate (the side where the chromatography strip is present) and inner side of the seal film (the side where the chromatography strip is present) must be able to be hot-sealed, i.e. they must contain materials that are hot-sealable. Examples of such hot-sealable materials for the seal film and substrate include a combination of a film having polyethylene (to be referred to as "PE" hereinafter) or PP on its inner side and a film whose inner side is coated with a corresponding hot melt adhesive or a combination of a film having PE on its inner side and a film having a PP-PE copolymer film on its inner side.

If the seal film is stuck on the substrate with paste, this may be effected by a combination of an optional seal film and a substrate having on its inner side a rubber, acrylic or vinyl ether polymer adhesive agent.

Close adhesion of the seal film and substrate should be made in such a manner that the substrate and seal film can be peeled off easily when used, at least at the position of the sample adding means. In order to effect easy peeling of the substrate and seal film and to keep proper sealing performance, a peeling strength of 1.5 to 2.0 kg weight per 15 mm width is desirable.

With regard to the seal film and substrate, (i) either the seal film or substrate has both a film containing a dehumidifying agent and a film containing an oxygen absorbing agent, (ii) the seal film has either a film containing a dehumidifying agent or a film containing an oxygen absorbing agent, and the substrate has the other film, (iii) either the seal film or substrate has either the film containing a dehumidifying agent or the film containing an oxygen absorbing agent, and the other has both the film containing a dehumidifying agent and the film containing an oxygen absorbing agent, (iv) both the seal film and substrate each have both the film containing a dehumidifying agent and the film containing an oxygen absorbing agent, (v) the seal film and the substrate both contain the same film which is either the film containing a dehumidifying agent or the film containing an oxygen absorbing agent, or (vi) either the seal film or substrate contains either the film containing a dehumidifying agent or the film containing an oxygen absorbing agent. When the seal film and/or substrate has the film containing a dehumidifying agent, the seal film and substrate are substantially water impermeable, at least at the portion where the seal film is not adhered closely to the substrate, and when the seal film and/or substrate has the film containing an oxygen absorbing agent, the seal film and substrate are substantially oxygen impermeable, at least at the portion where the seal film is not adhered closely to the substrate.

When the seal film has the film containing a dehumidifying agent, the seal film has a water impermeable layer on its outer side. Also, when the seal film has the film containing an oxygen absorbing agent, the seal film has an oxygen impermeable layer on its outer side. In the same manner, when the substrate has the film containing a dehumidifying agent, the substrate has a water impermeable layer on its outer side, and when the substrate has the film containing an oxygen absorbing agent, the substrate has an oxygen impermeable layer on its outer side. In many cases, the outermost side of the seal film is prepared in such a way that printing can be made thereon.

When the seal film and/or substrate does not have the film containing a dehumidifying agent and the film containing an oxygen absorbing agent, the seal film and/or substrate may be a single layer film or a multiple layer film which is obtained by an optional combination of an oxygen impermeable film, a water impermeable film, a film suited for hot sealing, an outermost PET film and the like.

When the substrate and seal film both have no oxygen absorbing agent-containing film, the substrate and seal film are not necessarily oxygen impermeable, and the substrate and seal film are not necessarily water impermeable when the substrate and seal film both have no dehumidifying agent-containing film. That is, it is not necessary to use a dehumidifying agent-containing film or water impermeable seal film and substrate when the chromatography strip is not degenerated by moisture, or to use an oxygen absorbing agent-containing film or oxygen impermeable seal film and substrate when the chromatography strip is not degenerated by oxygen.

The dehumidifying agent-containing film can be prepared by kneading a thermoplastic high molecular weight resin, preferably a polyolefin and more preferably one selected from low density polyethylene, linear low density polyethylene, ethylene-vinyloxide copolymers, ethylene acrylic acid copolymers, ethylene methacrylic acid copolymers, ethylene acrylic ester copolymers and ionomers based on acrylic and methacrylic acid copolymers, with an appropriate amount of calcium chloride, silica gel, molecular sieve, silicon dioxide, alumina, zeolite magnesium sulfate, gypsum and the like which are used as desiccating agents. Examples of the dehumidifying agent-containing films include those disclosed in Japanese Patent Publication 08-026348 (26348/96) incorporated herein by reference, "Moisture Guard" (manufactured by Toyo Seikan) and "Hiseat-Dry Film" (manufactured by Marutani Kakoki). A particularly preferred dehumidifying agent-containing film is 110 micrometer and composed of about 10 micrometer low density PE (LDPE), about 90 micrometer desiccant layer, containing varying amounts of a high molecular weight resin, such as LDPE, and a desiccating agent such as zeolite, molecular sieve and the like, and about 10 micrometer LDPE. Suitable dehumidifying agent-containing films preferably have a layer with a desiccating agent content between about 0.1 and 50% by weight, perferably between 10% and 50%. An overall desiccant content of between about 8 and 50 grams per meter squared is especially preferred. It is preferred to use a desiccant with an average particle size between about 5 and 70 microns to prepare the layer containing the desiccating agent.

The oxygen absorbing agent-containing film can be prepared by kneading a thermoplastic high molecular weight resin with an appropriate amount of active iron oxide, pyrogallol and the like oxygen absorbing agents. An example of an oxygen absorbing agent-containing film is "Oxy Guard" (manufactured by Toyo Seikan).

In some cases, the seal film is a film which has both a dehumidifying agent and an oxygen absorbing agent. Such a type of seal film can be called herein either a dehumidifying agent-containing film or an oxygen absorbing agent-containing film. In the same manner, the substrate may be a film which has both a dehumidifying agent and an oxygen absorbing agent. Such a type of substrate can be called herein either a dehumidifying agent-containing film or an oxygen absorbing agent-containing film.

Illustrative examples of the substrates which are substantially water impermeable include PE of 300 micrometer or more, PP of 300 micrometer or more, a multiple layer film consisting of, from the inner side, [PE or PP] of 300 micrometer or more and polyvinylidene chloride (to be referred to as "PVDC" hereinafter) of about 15 micrometer, and a multiple layer film consisting of, from the inner side, [PE or PP] of about 70 micrometer, PET of about 125 micrometer and PVDC of about 15 micrometer. Illustrative examples of substrates which are substantially water impermeable and contain a dehumidifying agent-containing film include "Moisture Guard" of 300 micrometer and a multiple layer film consisting of, from the inner side , "Moisture Guard" of about 110 micrometer, PET of about 125 micrometer and PVDC of about 15 micrometer. Illustrative examples of the substrates which are substantially oxygen impermeable include a multiple layer film consisting of, from the inner side, [PE or PP] of about 150 micrometer or more, polyvinyl alcohol saponificate of about 15 micrometer and [PE or PP] of 150 micrometer or more. The above examples are all transparent.

Illustrative examples of substrates which are substantially water and oxygen impermeable include a multiple layer film consisting of, from the inner side, [PE or PP] of 150 micrometer or more, PVDC of about 30 micrometer and [PE or PP] of 50 micrometer or more. Illustrative examples of substrates which are substantially water and oxygen impermeable and opaque include a multiple layer film consisting of, from the inner side, [PE or PP] of 200 micrometer or more, aluminum foil (to be referred to as "Al" hereinafter) of about 7 micrometer and PET of about 15 micrometer; a multiple layer film consisting of, from the inner side, [PE or PP] of 70 micrometer, PET of about 125 micrometer, Al of about 7 micrometer and PET of 12 micrometer; and a multiple layer film consisting of, from the inner side, [PE or PP] of about 70 micrometer, polystyrene of about 125 micrometer, Al of about 7 micrometer and PET of about 12 micrometer.

A preferred substrate consists of, from the inner side, about 30 micrometer of a layer that facilitates the removal of the seat film and is composed of a blend of PE and PP, about 188 micrometer white PET (for color contrast), about 7 micrometer Al (as an oxygen and moisture barrier) and about 12 micrometer PET. A particularly preferred substrate consists of, from the inner side, about 30 micrometer of a layer that facilitates the removal of the seal film and is composed of a blend of PE and PP, about 50 micrometer white PET, about 7 micrometer Al, and about 188 micrometer PET.

A substrate which is substantially water and oxygen impermeable and contains a dehumidifying agent- and/or oxygen absorbing agent-containing film can be obtained by replacing the inner film of the aforementioned multiple layer film which is substantially water and oxygen impermeable with "Moisture Guard" of 110 to 250 micrometer and/or "Oxy Guard" of 110 to 250 micrometer.

As occasion demands, pastes of rubber, acrylic or a vinyl ether polymer system may be applied to the sides, particularly inner side, of the substrate, In that case, release paper or release film is laminated on the paste-applied side until used. Paper, PET, PP or the like may be used as the release paper or release film with no particular limitation.

As illustrative examples of the seal film, those which are substantially water impermeable include a multiple layer film consisting of, from the inner side, [PE or PP] of about 70 micrometer and PET of about 12 micrometer. Those which are substantially oxygen impermeable include a multiple layer film consisting of, from the inner side, [PE or PP] of about 70 micrometer, polyvinyl alcohol saponificate of about 15 micrometer, PP of about 12 micrometer and PET of about 12 micrometer. Those which are substantially water and oxygen impermeable include a multiple layer film consisting of, from the inner side, [PE or PP] of about 70 micrometer, PVDC of about 30 micrometer and PET of about 12 micrometer. All of the above examples are transparent.

Illustrative examples of seal films which are substantially water impermeable and contain a dehumidifying agent-containing film include a multiple layer film consisting of, from the inner side, "Moisture Guard" of 110 micrometer and PET of about 12 micrometer (transparent) and a particularly preferred multiple layer film consisting of, from the inner side, "Moisture Guard" of about 110 micrometer, Al of about 7 micrometer and PET of about 12 micrometer (opaque). An illustrative example of a seal film which is substantially oxygen impermeable and contains an oxygen absorbing agent-containing film is a multiple layer film consisting of, from the inner side, "Oxy Guard" of 110 micrometer, Al of 7 micrometer and PET of 12 micrometer (opaque). An illustrative example of a seal film which is substantially water and oxygen impermeable and contains dehumidifying agent-containing film and oxygen absorbing agent-containing film is a multiple layer film consisting of, from the inner side, "Moisture Guard" of 110 micrometer, "Oxy Guard" of 110 micrometer, Al of about 7 micrometer and PET of 12 micrometer (opaque).

The multiple layer film can be produced by sticking its composing films together with an appropriate adhesive agent or by laminating parts of its composing films by means of co-extrusion and then, if necessary, by sticking the remaining composing materials together with an appropriate adhesive agent.

The chromatography immunoassay device can be produced by firstly preparing the aforementioned chromatography strips and, if necessary using a strip support and/or a protective laminate in the aforementioned manner, or preparing chromatography strips and simultaneously sticking a sample adding means and the like together, sealing the chromatography strip through tight adhesion of the aforementioned substrate to the seal film.

The chromatography immunoassay device of the present invention is used in the following manner. Only a single chromatography strip to be used is cut off, together with the substrate. The seal film, or at least a portion covering the sample adding means, is peeled off and a sample solution is added to the thus exposed sample adding means. In the case of a certain shape of the seal film, it may be necessary to peel off the whole portion of the seal film which covers the chromatography strip. When a plurality of chromatography strips are located on the substrate and a chromatography strip is used without first cutting it off, it is generally cut off after it is used. In some cases, the device may be used by separating the substrate from the strip support.

The present invention is further described with reference to the drawings. FIG. 1 is a schematic illustration showing an example of the chromatography immunoassay device of the present invention. In the drawing, a is a plan view, b is a sectional view and c is another sectional view. FIG. 2 is a schematic illustration showing an example of the chromatography strip. FIG. 3 is a schematic illustration showing another example of the chromatography immunoassay device of the present invention. In these drawings, 1 indicates a chromatography strip, 2 indicates a substrate, 3 indicates a seal film, 4 indicates a chromatography carrier, 5 indicates a sample adding means, 6 indicates a labeling means, 7 indicates a detecting means, 8 indicates a strip support, 9 indicates a protective laminate, 10 indicates a perforation and 11 (slant lines) indicates closely adhered portions of the substrate and seal film.

The chromatography strip 1 is located on the substrate 2, and, together with a dehumidifying agent- and/or oxygen absorbing agent-containing film, the chromatography strip 1 is sealed and isolated from the air by closely adhering the seal film 3 to the chromatography strip peripheral area 11 of the substrate 2 (FIG. 1).

When a comb type substrate is used as shown in FIG. 3, the sample adding means of each chromatography strip is completely isolated so that there is no possible danger of a sample solution flowing into an adjacent chromatography strip by mistake when the sample is added.

The chromatography strip 1 is constructed by arranging the sample adding means 5, labeling means 6 and detecting means 7 on the chromatography carrier 4 (FIG. 2). As occasion demands, the chromatography strip is supported or protected by the strip support 8 and protective laminate 9.

The perforation 10 is optionally arranged when required, in order to effect easy cut off of a single chromatography strip from the chromatography immunoassay device when a plurality of chromatography strips are located on the substrate. The perforation 10 may be used in such a manner that a single chromatography strip can be cut off or several chromatography strips can be cut off simultaneously.

Figure 1:
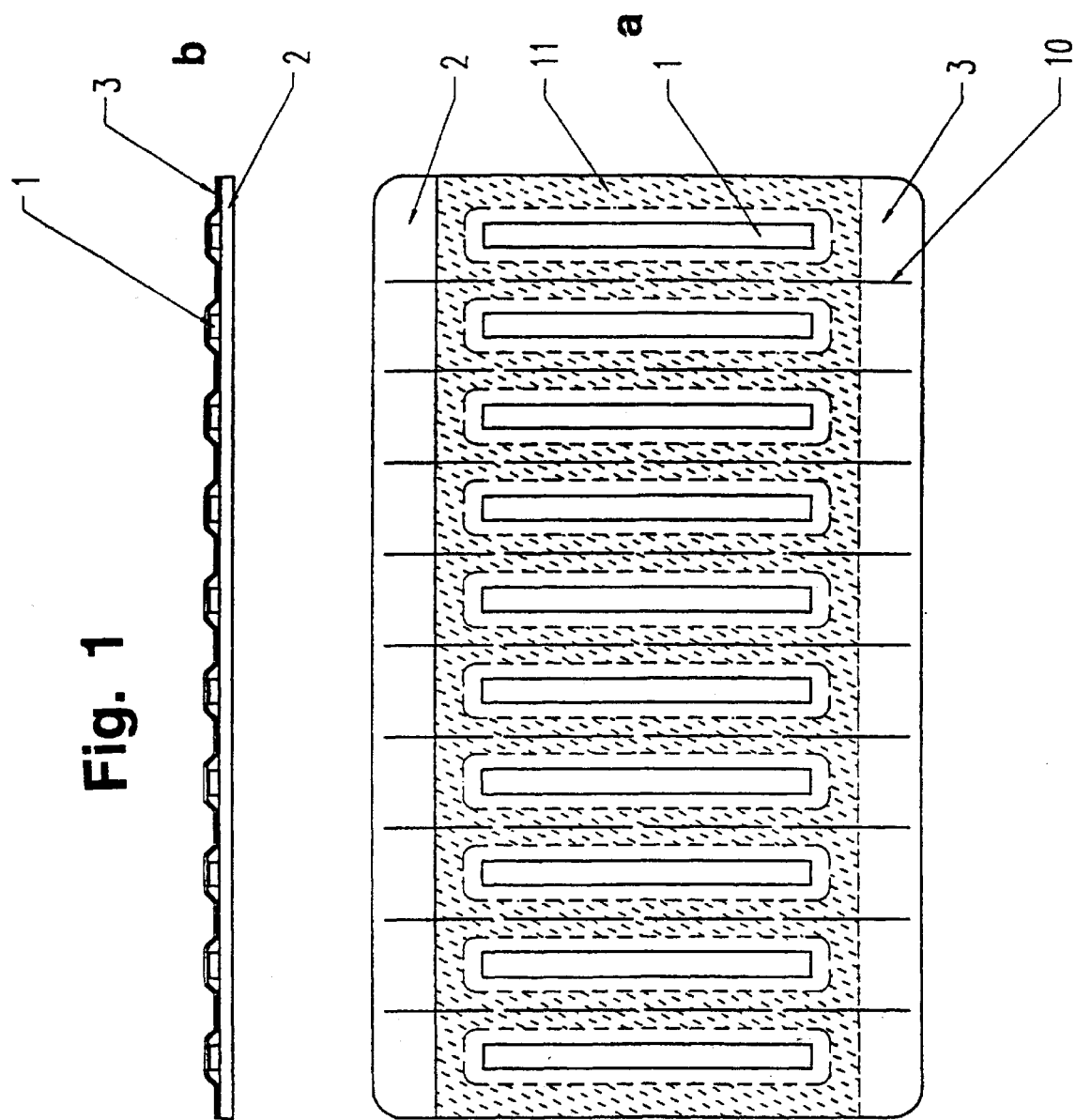
FIG. 1 is a schematic illustration showing an example of the chromatography immunoassay device of the present invention, in which a is a plan view, b is a side elevation view and c is an elevation view.
Figure 2:
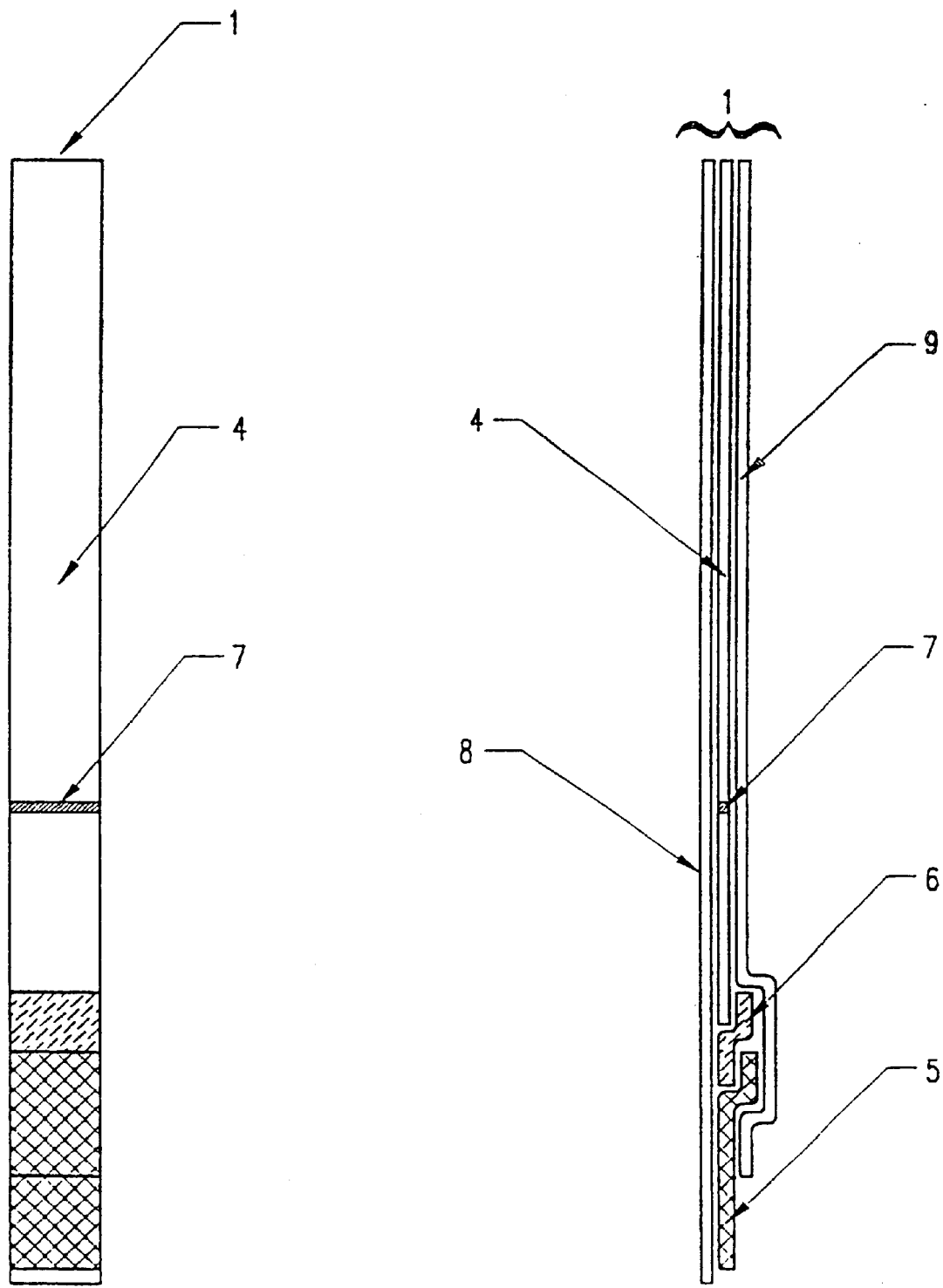
FIG. 2 is a schematic illustration showing an example of the chromatography strip.
Figure 3:
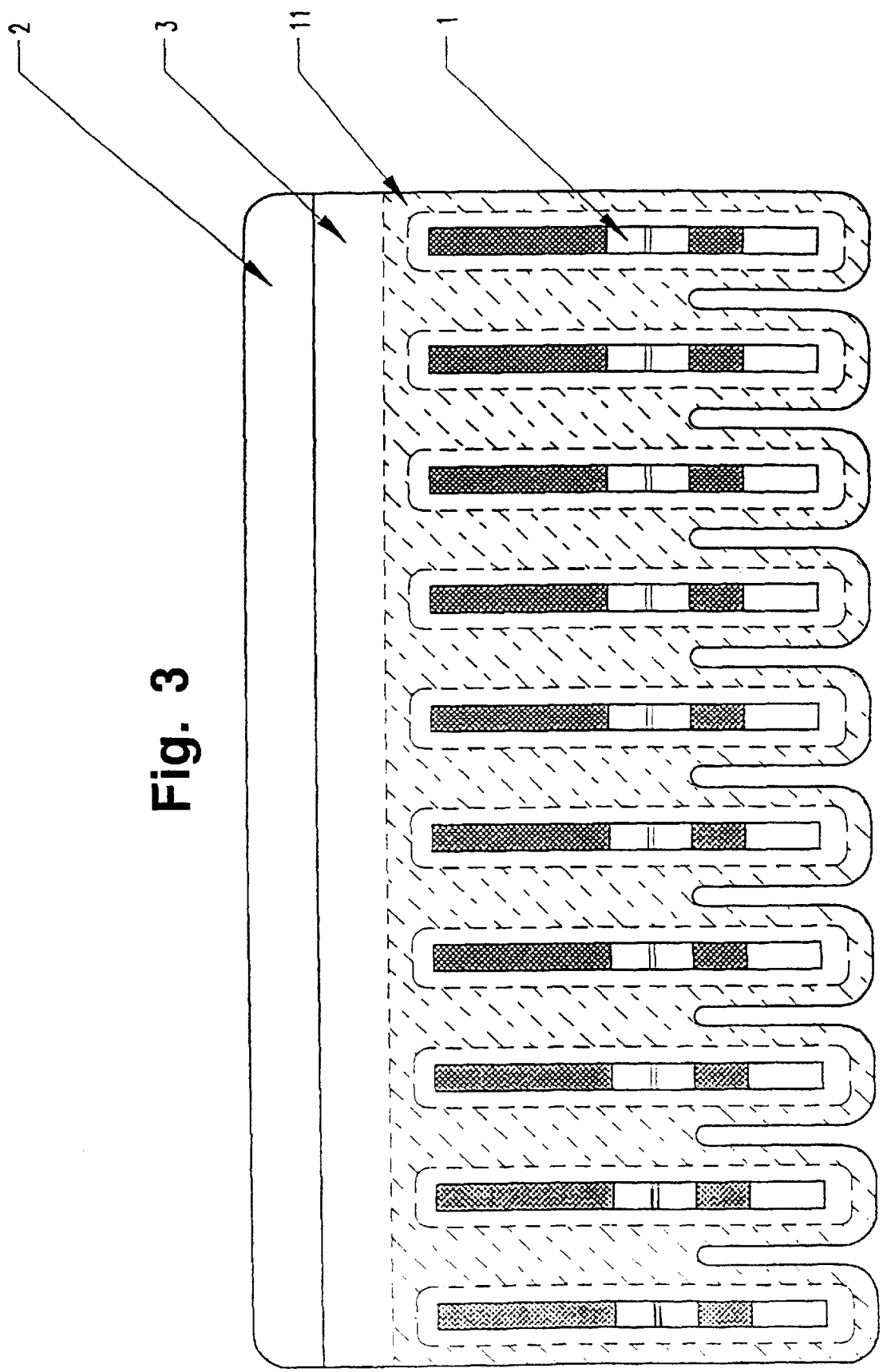
FIG. 3 is a schematic illustration showing another example of the chromatography immunoassay device of the present invention.

DESCRIPTION OF MARKS 1 a chromatography strip
2 a substrate
3 a seal film
4 a chromatography carrier
5 a sample adding means
6 a labeling means
7 a detecting means
8 a strip support
9 a protective laminate
10 a perforation
11 closely adhered portion of the substrate and seal film

EXAMPLES

Example 1

Performance of Seal Film and Substrate Combinations

Combinations of seal films and substrates, shown in Table 1, were prepared. Each multiple layer film was prepared by sticking respective single layer films together with an adhesive agent.

TABLE 1

| Sample No. | Seal film | Substrate |
|---|---|---|
| 1 | MG/Al/PET$_{12}$ | PP70/PET$_{125}$/Al/PET$_{12}$ |
| 2 | MG/PVDC/PET$_{12}$ | PP$_{300}$ |
| 3 | MG/Al/PET$_{12}$ | MG/PET$_{125}$/Al/PET$_{12}$ |
| 4 | MG/OG/Al/PET$_{12}$ | PP$_{70}$/PET$_{125}$/Al/PET$_{12}$ |
| 5 | OG/Al/PET$_{12}$ | MG/PET$_{125}$/Al/PET$_{12}$ |
| 6 | MG | PP$_{300}$ |
| 7 (control) | PP70/Al/PET$_{12}$ | PP$_{70}$/PET$_{125}$/Al/PET$_{12}$ |

MG: 110 micrometer "Moisture Guard" (manufactured by Toyo Seikan)
OG: 110 micrometer "Oxy Guard" (manufactured by Toyo Seikan)
Al: 7 micrometer Al
PET$_{12}$: 12 micrometer PET
PET$_{125}$: 125 micrometer PET
PP$_{70}$: 70 micrometer PP
PP$_{300}$: 300 micrometer PP
PVDC: 12 micrometer PVDC A. Dehumidifying performance test 1 Seal films of samples 1, 2, 3, 4 and 7, substrates of samples 3 and 5 and commercially available packaged granular silica gel, in respective amounts shown in Table 2, were stored for 3 days at room temperature (23° C., humidity 40%) or in a constant temperature oven of 40° C. Thereafter, the weight of each sample was measured, and increased amount from the initial weight was used as the amount of water absorption. The results are shown in Table 2.

It is evident from these results that the films having a dehumidifying agent-containing film had high dehumidifying capacity.

TABLE 2

| | Quantity | Absorbed water (mg) | |
|---|---|---|---|
| Sample | of sample | 23° C. | 40° C. |
| Seal film of sample 1 | 300 cm$^2$ | 84.2 | 79.7 |
| Seal film of sample 2 | 300 cm$^2$ | 84.0 | 79.5 |
| Seal film of sample 3 | 300 cm$^2$ | 83.5 | 78.9 |
| Seal film of sample 4 | 300 cm$^2$ | 83.7 | 78.6 |

TABLE 2-continued

| | Quantity | Absorbed water (mg) | |
|---|---|---|---|
| Sample | of sample | 23° C. | 40° C. |
| Substrate of sample 3 | 300 cm$^2$ | 84.9 | 80.3 |
| Substrate of sample 5 | 300 cm$^2$ | 84.1 | 79.9 |
| Packaged granular silica gel (control) | 5 g | 892 | 288 |
| Seal film of sample 7 (control) | 30 cm$^2$ | 0.1 | −0.1 |

The above study was repeated comparing the absorptive capacity of silica gel (5 g package) with the seat film of sample 1 or 3 containing either 0.75 g (seal film A) or 1.50 g of desiccant/300 cm$^2$ (seal film B). Storage conditions were for 6 days at 24° C. with 50% relative humidity, 40° C. with 20% relative humidity, or 2–8° C. with 90% relative humidity. Samples were also stored for 19 days at 2–8° C. with 90% relative humidity. Results (Table 3) were calculated as above (mg of water absorbed) and also as g water absorbed/g of desiccant %. As can be seen from these results, the films have a high moisture absorbing, dehumidifying capacity. Also, film B, which contains twice as much desiccant as film A, is capable of absorbing roughly twice as much water as film A.

TABLE 3

| | Storage Condition | Storage Time | Absorbed Water | |
|---|---|---|---|---|
| Sample | (Temp/Rel humidity) | (Days) | (mg) | (g/g %) |
| Seal Film A | 40° C./20% | 6 | 129 | 17.26 |
| " | 24° C./50% | 6 | 141 | 18.78 |
| " | 2–8° C./90% | 6 | 76 | 10.17 |
| " | 2–8° C./90% | 19 | 144 | 19.13 |
| Seal Film B | 40° C./20% | 6 | 268 | 17.84 |
| " | 24° C./50% | 6 | 292 | 19.45 |
| " | 2–8° C./90% | 6 | 121 | 8.06 |
| " | 2–8° C./90% | 19 | 277 | 18.47 |
| Silica gel | 40° C./20% | 6 | 495 | 9.9 |
| " | 24° C./50% | 6 | 1472 | 29.44 |
| " | 2–8° C./90% | 6 | 1857 | 37.15 |
| " | 2–8° C./90% | 19 | 1937 | 38.74 |

B. Dehumidifying performance test 2 Bags were prepared (inner surface area, 600 cm$^2$) using the seal films of samples 1, 2, 3, 4 and 6 and substrates of samples 3 and 5 (see Table 1), and three sides of the bags were hot-sealed. A piece of humidity indicator paper manufactured by Humidial Company, U.S.A., was put into each bag and then the remaining side was hot-sealed. A similar bag (inner surface area, 600 cm$^2$) was prepared using the seal film of sample 7. The humidity indicator paper described above and 2 g of packaged granular silica gel were put into the bag and the remaining side was hot-sealed. As a control, similar bag (inner surface area, 600 cm$^2$) was prepared using the seal film of sample 7, the humidity indicator paper described above was put into the bag and then the remaining side was sealed by hot sealing. The thus prepared bags were allowed to stand for 3 days at room temperature and then opened, with the humidity indicator paper read immediately on opening the bag.

The humidity indication was 45% in the control bag and 15% or less in all other bags. The minimum humidity measurable with this humidity indicator paper is 15%.

C. Oxygen absorption performance test Bags were prepared (inner surface area, 600 cm$^2$) using the seal films of samples 4 and 5 (see Table 1), and the four sides of each bag were were hot-sealed. A piece of natural rubber, having a size of 1×1 cm, was stuck on the surface of the bag with an adhesive agent. Using a syringe, air was completely sucked out of the bag through the natural rubber piece and then 20 ml of air was accurately injected. After 3 days of standing at room temperature, a portion of the air in the bag was taken out through the natural rubber piece to measure its oxygen concentration using gas chromatography with a column packed with molecular sieve.

Oxygen was not detected in any of the bags tested. The oxygen concentration detection limit in this assay system is 0.01%. It is evident from the results that the multiple layer film having an oxygen absorbing agent-containing film has oxygen absorbing capacity.

On the basis of the above results, it can be expected that the chromatography immunoassay device produced by the method described in Example 2 below using the sample 1, 2, 3, 4, 5 or 6 seal films and substrates will have a high dehumidifying capacity. It can be expected that the chromatography immunoassay device produced using the sample 4 or 5 seal films and substrates will also have a high oxygen absorbing capacity.

Example 2

Chromatography Immunoassay Device Stability

A. Production of the device A labeled substance comprised of an anti-human hemoglobin antibody labeled with selenium colloid was prepared in the following manner. First, selenium colloid was prepared by stirring 91 mM of sodium L-ascorbate and 32 mM of selenium oxide at about 4° C. for 15 minutes and then at about 42° C. for about 70 hours. The thus obtained selenium colloid was diluted with 10 mM bis-tris buffer, pH 7.0 to an absorbance of 15 at 550 nm. The resulting dilution was mixed with mouse monoclonal anti-human hemoglobin antibody (0.02%) and stirred at room temperature for 1 hour. The thus obtained selenium colloid-labeled anti-human hemoglobin antibody was washed with 10 mM Tris-HCl buffer, pH 7.2 and used as the labeled substance.

A labeling means was prepared in the following manner: the labeled substance was added to 10 mM Tris-HCl buffer, pH 7.2 containing 1% casein, and the absorbance at 550 nm was adjusted to 1.0 to obtain a labeled substance suspension. A glass fiber membrane (Lypore 9524, manufactured by LYDALL, U.S.A.) was soaked in the thus obtained suspension and sufficiently impregnated therewith and then the glass fiber membrane was dried to be used as the labeling means.

A detecting means was prepared in the following manner: a mouse monoclonal anti-human hemoglobin antibody, whose binding site to human hemoglobin is different from that of the aforementioned anti-human hemoglobin antibody, was added to 30 mM Tris-HCl buffer, pH 7.4 containing 150 mM sodium chloride at a final concentration of 2 mg/ml. Separately from this, as a chromatography carrier, a rectangular 0.4×4.5 cm piece of nitrocellulose membrane (manufactured by Schleicher & Schuell, U.S.A.) having a pore size of 5 micrometer was stuck on a strip support (PE PET100 PE LR007A, manufactured by Lintech) having a rectangular size of 0.4×6.0 cm and a thickness of 100 micrometer, in such a manner that the downstream ends of both pieces matched with each other when the longer sides were arranged longitudinally. A solution mixed with the antibody (anti-human hemoglobin antibody) was added dropwise to the nitrocellulose membrane stuck on the strip support, forming a line at a position about 1 cm from the upstream end of the membrane. This was allowed to dry sufficiently so as to fix the anti-human hemoglobin antibody to the nitrocellulose.

A chromatography strip was prepared in the following manner. The aforementioned labeling means was cut into a square piece of 0.4×0.4 cm and stuck on the strip support upstream of the detecting means containing the anti-human hemoglobin-fixed nitrocellulose membrane, in such a manner that it slightly touched the nitrocellulose membrane. As a sample adding means, non-woven fabric (Sontara 8801, manufactured by Du Pont) cut to a size of 0.4×1.3 cm was stuck on the strip support upstream of the labeling means in such a manner that it slightly touched the labeling means. On this was further stuck a protective film (PET25 PE LR007A, manufactured by Lintech) having a rectangular size of 0.4×5.1 cm, in such a manner that its upper end matched with that of the nitrocellulose membrane when their longer sides were arranged longitudinally, thereby obtaining the chromatography strip.

The chromatography strip was stuck on to the substrate in the following manner: the rear face of the strip support of each of a total of 10 chromatography strips was stuck on the substrate of sample 1 or 7 (see Table 1), at 1.8 cm intervals, in parallel, by uniformly arranging their upper ends.

The seal film was closely stuck on the substrate by hot sealing in the following manner: the substrate on which the chromatography strips had been stuck was divided into two equal portions, and one of the portions was hot-sealed with the seal film of sample 1 in such a manner that a 0.25 cm peripheral range around each chromatography strip was not hot-sealed. The hot sealing was carried out at a sealing temperature of 120° C., for a sealing period of 1.5 seconds and under a sealing pressure of 3.0 kg/cm$^2$. This was further divided into two portions, and one of them was punched as shown in FIG. 1 using a cutting die. This was used as device A. Using another cutting device, the remaining portion was made into device B having one chromatography strip.

As a control, the remaining portion of the substrate on which 5 chromatography strips had been stuck, together with 5 g of commercially available packaged granular silica gel, were put into a bag (25×15 cm in size) obtained by hot-sealing three sides of sample 7 seal film, and the resulting bag was hot-sealed. This was used as device C.

As another control, the substrate of sample 6 on which the chromatography strip had been stuck, was hot-sealed with the seal film of sample 7 in the same manner as described above, to be used as device D.

B. Storage under severe conditions The thus prepared devices A, B, C and D were allowed to stand for 1 day at 25° C. under a relative humidity of 60% and then for 28 days at 40° C. under a relative humidity of 70%. After storage of the devices A, B, C and D under such severe conditions, they were allowed to stand for 2 hours at 25° C. and then the devices A, B and D as such, and the device C after opening, were allowed to stand for 24, 48 and 96 hours at 25° C. under a relative humidity of 60%, with the devices exposed to the outside air.

A sample solution was prepared by dissolving 0, 5, 10, 25, 50, 100, 200 or 500 ng/ml of human hemoglobin (manufactured by Sigma, U.S.A.), 0.1% of bovine serum albumin (manufactured by Seikagaku Kogyo), 0.9% sodium chloride and 0.1% sodium azide in 0.1 M Tris-HCl buffer, pH 7.6. A 25 µl portion of the thus prepared sample solution was added to the chromatography strip sample adding means of each of the devices A, B, C and D before, just after or after 24, 48 or 96 hours of their storage under the severe conditions. The results were judged by reading the selenium colloid-originated "redness", which would result if a sample was detected as positive on the detecting means of the strip, by the naked eye 7 minutes after the addition of the sample solution. Sensitivity was based on the minimum hemoglobin concentration at which the "redness" was observed by the naked eye. The results are shown in Table 4.

TABLE 4

Before/after storage under severe conditions

| Device | before | just after | 24 hrs after | 48 hrs after | 96 hrs after |
|---|---|---|---|---|---|
| A | 25 ng/ml | 25 ng/ml | 25 ng/ml | 25 ng/ml | 25 ng/ml |
| B | 25 ng/ml | 25 ng/ml | 25 ng/ml | 25 ng/ml | 25 ng/ml |
| C | 25 ng/ml | 25 ng/ml | 25 ng/ml | 50 ng/ml | 100 ng/ml |
| D | 25 ng/ml | 200 ng/ml | 200 ng/ml | 500 ng/ml | 500 ng/ml |

As is evident from Table 4, the chromatography strips of the devices A, B and C just after their storage under the severe conditions showed the same sensitivity as the chromatography strips before storage under the severe conditions, and their stability during the severe condition storage was excellent. As the storage period under the severe conditions progressed to 24 hours, 48 hours and then to 96 hours, sensitivity of the devices A and B did not change, but sensitivity of the device C decreased gradually. This shows that the unsealed device C had poor stability. The device D which had no dehumidifying agent-containing film nor desiccating agent showed considerable reduction of its sensitivity by the severe condition test.

As can be understood from this test, conventional products cannot be preserved at room temperature after some of the chromatography strips are used, thus requiring storage in a cold room. A device which is produced by conventional means cannot be run quickly, e.g. if emergency testing were required, after storage in a cold room, since it is first necessary to warm the device to room temperature in order to carry out the assay. However, device A can cope with emergency situations because of its ability to be stored at room temperature. Also, it can be used with confidence, because stability of its chromatography strips is guaranteed until its seal film is peeled off. Since the seal film can be peeled off easily, using device A requires hardly any labor.

With regard to the production cost, the prior art products require packaging and sealing of the produced device together with a dehumidifying agent and the like in a bag, which is substantially impermeable to water and the like, while device A does not require such handling so that its production cost can be reduced greatly, off setting a slight increase in the cost of its substrate and seal film. The manpower, and associated costs, needed to produce device A should also be lower than current products.

C. One Month Stability Chromatography strips for the detection of human hemoglobin were prepared as in Example 2.A. above and 13 strips were packaged either in an aluminium pouch with no desiccant (A), packaging with 67.8 cm$^2$ of a seal film consisting of 110 micrometer MG (made up of 10 micrometer PE/PS (PS is defined herein as polystyrene), 90 micrometer desiccant layer containing 11.9 g/m$^2$ and 10 micrometer PE/PS)/15 micrometer Al/12 microMolar PET (B), packaging with 678.6 cm$^2$ of the same seal film (C) or in an aluminium pouch with conventional desiccant consisting of 1.3 g Silica gel (D). All strips were exposed overnight to 65% relative humidity at 25° C. before packaging and heat sealing. The silica gel and seal film used were exposed to 65% relative humidity at 25° C. for 6 hours before being used.

After the strips were heat sealed under the packaging conditions described above, they were stored in a 25° C. incubator and tested 16 and 29 days later (25C storage), or were stored for one day in a 25° C. incubator, then moved to a 37° C. incubator and tested 15 and 28 days after being moved to 37° C. (37C storage).

Testing was done as in B. above using samples containing 0 (negative control), 10, 25, 50, 100 or 500 ng/ml of human hemoglobin. Results were read 7 minutes after sample was added and are reported in Table 5 as the minimum hemoglobin concentration at which the signal could be observed by the naked eye.

TABLE 5

| | Test Sensitivity (ng/ml) with: | | | |
|---|---|---|---|---|
| Packaging | 25 C. storage | | 37 C. storage | |
| Condition | 16 days | 29 days | 16 days | 29 days |
| A (no desiccant) | 25 | 50 | 100 | 500 |
| B (1× seal film) | 25 | 25 | 25 | 25 |
| C (10× seal film) | 25 | 25 | 25 | 25 |
| D (Silica gel) | 25 | 25 | 25 | 25 |

Strips packaged without any desiccant showed poor sensitivity and thus poor stability after storage for one month at either 25° C. or 37° C. No decrease in test sensitivity was seen under either storage condition, when strips were packaged with desiccant. Strips that were packaged with seal film containing desiccant maintained similar performance to strips packaged with silica gel, with the 1× seal film performing as well as when 10 times more seal film was used. Thus, the seal film containing desiccant is able to maintain test sensitivity and shows good stability under storage conditions up to one month.

Example 3

HIV Chromatography Immunoassay Device Long Term Stability

Chromatography strips were prepared in a manner similar to Example 2.A. above except with appropriate modifications to allow for the detection of HIV antibody, e.g. the labeling means used was a commercially available polyclonal or monoclonal antibody to the heavy and/or light chain of human IgG, and the detecting means used was HIV antigen. Twenty-two strips were packaged either in an aluminium pouch with 5 g of silica gel as the desiccant (A), in an aluminium pouch with 2.2 g of silica gel as desiccant (B), in an aluminium pouch with no desiccant (C), by application to a substrate consisting of 12 micrometer PET, 7 micrometer Al, 188 micrometer PET, 12 micrometer white PET and a peelable layer made of blended PE, and covered with the seal film of sample 1 or 3 (Table 1) containing either 25 g/m$^2$ (D) or 50 g/m$^2$ (E) of desiccant. The strips, silica gel and seal film used were exposed to 65% relative humidity at 27° C. for 6 hours before use. The strips, packaged under the 5 conditions stated, were then heat sealed.

After the strips were heat sealed under the packaging conditions described above, they were stored in a 25° C. incubator for one day then moved either to a 30° C. incubator, a 45° C. incubator or to a 45° C. controlled box with 65% relative humidity. Strips were removed and tested after 0.5, 1, 3 and 6 months of storage.

Testing was done as in Example 2.B. above, in duplicate, using normal human serum/plasma as a negative control and human serum/plasma from HIV-1 and HIV-2 infected individuals as positive samples containing HIV-1 or HIV-2 antibody, respectively. Two-fold serial dilutions were made of the HIV-1 and HIV-2 samples, and five 2-fold dilutions, ranging from $2^{11}$ to $2^{15}$ for HIV-1, and $2^{10}$ to $2^{14}$ for HIV-2, were tested. Results were read 15 minutes after sample was added and are reported in Tables 6, 7 and 8 as the highest HIV sample dilution at which the signal could be observed by the naked eye. All negative control samples gave negative results with all strips at all packaging and storage conditions.

TABLE 6

Test Sensitivity ($2^x$ Dilution) after 30° C. Storage

| Time | HIV-1 | | | | | HIV-2 | | | | |
|---|---|---|---|---|---|---|---|---|---|---|
| (mos): | 0 | 0.5 | 1 | 3 | 6 | 0 | 0.5 | 1 | 3 | 6 |
| Pkg | | | | | | | | | | |
| A | 13 | 13 | 13 | 13 | 13/14 | 12 | 12 | 12 | 12 | 12 |
| B | 13 | 13 | 13/14 | ND | ND | 12 | 12 | 12 | ND | ND |
| C | 13 | 13 | 12 | ND | ND | 12 | 12 | 11 | ND | ND |
| D | 13 | 13/14 | 13 | 13 | 13/14 | 12 | 12 | 12 | 12 | 12 |
| E | 13 | 13 | 13 | 13 | 14 | 12 | 12 | 12 | 12 | 12 |

(ND = not determined)

TABLE 7

Test Sensitivity ($2^x$ Dilution) after 45° C. Storage

| Time | HIV-1 | | | | | HIV-2 | | | | |
|---|---|---|---|---|---|---|---|---|---|---|
| (mos): | 0 | 0.5 | 1 | 3 | 6 | 0 | 0.5 | 1 | 3 | 6 |
| Pkg | | | | | | | | | | |
| A | 13 | 13 | 13 | 13 | 13 | 12 | 12 | 12 | 12 | 12 |
| B | 13 | 13 | 13 | ND | ND | 12 | 12 | 11 | ND | ND |
| C | 13 | <11 | <11 | ND | ND | 12 | <10 | <10 | ND | ND |
| D | 13 | 13 | 13 | 13 | 13 | 12 | 12 | 12 | 12 | 12 |
| E | 13 | 13 | 13 | 13 | 13 | 12 | 12 | 12 | 12 | 12 |

(ND = not determined)

TABLE 8

Test Sensitivity ($2^x$ Dilution) after 45° C./65% Rel Humidity Storage

| Time | HIV-1 | | | | | HIV-2 | | | | |
|---|---|---|---|---|---|---|---|---|---|---|
| (mos): | 0 | 0.5 | 1 | 3 | 6 | 0 | 0.5 | 1 | 3 | 6 |
| Pkg | | | | | | | | | | |
| A | 13 | 13 | 13 | 13 | 13 | 12 | 12 | 12 | 12 | 12 |
| B | 13 | 13 | 13 | ND | ND | 12 | 12 | 12 | ND | ND |
| C | ND | ND | ND | ND | ND | ND | ND | ND | ND | ND |
| D | 13 | 13 | 13 | 13 | 13 | 12 | 12 | 12 | 12 | 12 |
| E | 13 | 13 | 13 | 13 | 13 | 12 | 12 | 12 | 12 | 12 |

(ND = not determined)

Chromatography strips packaged without any desiccant (C) showed the poorest performance, with loss of sensitivity over time in storage, under all conditions tested. Strips packaged with the higher level of silica gel desiccant (5 g) or with seal film containing desiccant, maintained performance over 6 months of storage under all conditions tested. Both levels of desiccant used in the seal film were equally effective. Thus, the seal film containing desiccant is able to maintain the test sensitivity of the chromatography assay device stored within it, and shows good performance and stability under long term storage conditions.

While the invention has been described in each of its various embodiments, it is expected that certain modifications thereto may be effected by those skilled in the art without departing from the true spirit and scope of the invention as set forth in the specification and accompanying claims.

What is claimed is:

1. An immunochromatographic assay device in which:
  (1) one or more chromatographic strips having at least a sample addition site and a detection site are spaced apart from one another and placed on a substrate comprising a flat plate or without a strip support interposed therebetween;
  (2) a sealing film is placed on said chromatographic strips with or without a protective laminate interposed therebetween to cover all the chromatographic strips;
  (3) portions of said substrate and sealing film are adhered around each of the chromatographic strips to seal each chromatographic strip;
  (4) said adhesion between the sealing film and the substrate is such that the sealing film may easily be peeled off from the substrate at least at the sample addition site;
  (5) (i) either the sealing film or the substrate comprises either or both of a desiccant-containing film and an oxygen absorbent-containing film; or (ii) the sealing film comprises either of a desiccant-containing film or an oxygen absorbent-containing film while the substrate comprises the other film, or (iii) either of the sealing film or the substrate comprises either of a desiccant-containing film or an oxygen absorbent-containing film while the other comprises both a desiccant-containing film and an oxygen absorbent-containing film, or (iv) both the sealing film and the substrate comprise either or both of desiccant-containing film and an oxygen absorbent-containing film; and (6) when the sealing film and/or the substrate comprise desiccant-containing film, the sealing film and the substrate are substantially impermeable to water at least at portions other than said adhered portions; or when the sealing film and/or the substrate comprise an oxygen absorbent-containing film, the sealing film and the substrate are substantially impermeable to oxygen at least at portions other than said adhered portions.

2. The immunochromatographic assay device of claim 1, wherein the chromatographic strip additionally has a labeling site, the labeling site is located at a site selected from a group consisting of the sample addition site, and a site along the chromatographic strip between the sample addition site and the detection site.

3. The immunochromatographic assay device of claim 1, wherein the sealing film is a multilayer film comprising a metallic film.

4. The immunochromatographic assay device of claim 1, wherein the substrate is a multilayer film comprising a metallic film.

5. The immunochromatographic assay device of claim 3, wherein the metallic film is an aluminum foil.

6. The immunochromatographic assay device of claim 4, wherein the metallic film is aluminum foil.

7. The immunochromatographic assay device of claim 1, wherein 5 to 12 chromatographic strips are placed on the substrate.

8. The immunochromatographic assay device of claim 1, wherein the sealing film and the substrate are adhered by heat sealing.

9. An immunochromatographic assay device resistive to environmental degradation by the action of water or oxygen comprising a sheet material capable of supporting capillary flow on which is immobilized a biological reagent capable of a reaction with a specific reaction partner under ambient conditions packaged between two generally flat materials which are sealed together in a manner which allows them to be easily at least partially separated to expose at least a portion of the capillary flow sheet wherein at least one of said flat materials carries a desiccant-containing film or an oxygen absorbent containing film or both on the surface which faces the capillary flow sheet.

10. The assay device of claim 9 wherein at least one of the flat materials carries at least a desiccant-containing film and both flat materials are substantially impermeable to water at least at the portions other than those at which they are adhered to one another.

11. The assay device of claim 10 wherein a labeled biological reagent capable of a reaction with a specific reaction partner under ambient conditions is deposited on the capillary flow sheet in a manner which allows it to be carried along with a liquid sample being moved along said flow sheet by capillary action.

12. The assay device of claim 11 wherein the label is a colored substance which becomes visible if a sufficient amount is accumulated at the immobilized biological reagent as a result of conducting an assay.

13. An immunochromatographic assay device in which:

(1) one or more chromatographic strips having at least a sample addition site and a detection site are spaced apart from one another and placed on a substrate comprising a flat plate or without a strip support interposed therebetween;

(2) a sealing film is placed on said chromatographic strips with or without a protective laminate interposed therebetween to cover all the chromatographic strips;

(3) portions of said substrate and sealing film are adhered around each of the chromatographic strips to seal each chromatographic strip;

(4) said adhesion between the sealing film and the substrate is such that the sealing film may easily be peeled off from the substrate at least at the sample addition site;

(5) either the sealing film or the substrate or both the sealing film and the substrate comprise a desiccant-containing film; and (6) when the sealing film and/or the substrate comprise the desiccant-containing film, the sealing film and the substrate are substantially impermeable to water at least at portions other than said adhered portions.

14. An immunochromatographic assay device in which:

(1) one or more chromatographic strips having at least a sample addition site and a detection site are spaced apart from one another and placed on a substrate comprising a flat plate or without a strip support interposed therebetween;

(2) a sealing film is placed on said chromatographic strips with or without a protective laminate interposed therebetween to cover all the chromatographic strips;

(3) portions of said substrate and sealing film are adhered around each of the chromatographic strips to seal each chromatographic strip;

(4) said adhesion between the sealing film and the substrate is such that the sealing film may easily be peeled off from the substrate at least at the sample addition site;

(5) either the sealing film or the substrate, or both the sealing film and the substrate comprise an oxygen absorbent-containing film; and (6) when the sealing film and/or the substrate comprise the oxygen absorbent-containing film, the sealing film and the substrate are substantially impermeable to oxygen at least at portions other than said adhered portions.

* * * * *